(12) United States Patent
Park et al.

(10) Patent No.: US 10,378,032 B2
(45) Date of Patent: Aug. 13, 2019

(54) **MICROORGANISM OF THE GENUS *ESCHERICHIA* PRODUCING L-TRYPTOPHAN AND A METHOD FOR PRODUCING L-TRYPTOPHAN USING THE SAME**

(71) Applicant: CJ Cheiljedang Corporation, Seoul (KR)

(72) Inventors: Hye Min Park, Gyeonggi-do (KR); Baek Seok Lee, Seoul (KR); Seok Myung Lee, Seoul (KR); Kyungrim Kim, Seoul (KR); Kwang Ho Lee, Daejeon (KR); Ki Yong Cheong, Gyeonggi-do (KR); Keun Cheol Lee, Gyeonggi-do (KR); Hyeongpyo Hong, Gangwon-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/573,244

(22) PCT Filed: May 10, 2016

(86) PCT No.: PCT/KR2016/004894
§ 371 (c)(1),
(2) Date: Nov. 10, 2017

(87) PCT Pub. No.: WO2016/182322
PCT Pub. Date: Nov. 17, 2016

(65) Prior Publication Data
US 2018/0127792 A1    May 10, 2018

(30) Foreign Application Priority Data
May 14, 2015   (KR) .................. 10-2015-0067659

(51) Int. Cl.
*C12P 13/22*      (2006.01)
*C12N 15/71*      (2006.01)
*C12N 9/16*       (2006.01)
*C12P 13/14*      (2006.01)

(52) U.S. Cl.
CPC .............. *C12P 13/227* (2013.01); *C12N 9/16* (2013.01); *C12N 15/71* (2013.01); *C12P 13/14* (2013.01); *C12Y 301/03* (2013.01)

(58) Field of Classification Search
None
See application file for complete search history.

(56) References Cited

FOREIGN PATENT DOCUMENTS

| KR | 10-2005-0059685 | 6/2005 |
| KR | 10-2009-0075549 | 7/2009 |
| KR | 10-2013-0082121 | 7/2013 |
| RU | 2007133293 A | 3/2009 |

OTHER PUBLICATIONS

Accession P0A8Y6. Jun. 21, 2005 (Year: 2005).*
Akashi H. et al., Metabolic efficiency and amino acid composition in the proteomes of *Escherichia coli* and Bacillus subtilis, Proc. Natl. Acad. Sci. USA, Mar. 19, 2002, pp. 3659-3700, vol. 99, No. 6.
Datsenko Ad et al., One-step inactivation of chromosomal genes in *Escherichia coli* K-12 using PCR products, Proc. Natl. Acad. Sci. USA, Jun. 6, 2002, pp. 6640-6645, vol. 97, No. 12.
Gosset G., Production of aromatic compounds in bacteria, Current Opinion in Biotechnology, 2009, pp. 651-658, vol. 20.
Gu P. et al., One-step of tryptophan attenuator inactivation and promoter swapping to improve the production of L-tryptophan in *Escherichia coli*, Microbial Cell Factories, 2012, vol. 11, No. 30.
Hara et al., Glutathione production by efficient ATP-regenerating-regenerating *Escherichia coli* mutants, Federation of European Microbiological Societies, Blackwell Publishing Ltd., 2009, pp. 217-224, vol. 297.
Wang M., Evolution of Structure and Function Among Hotdog-Fold Thioesterases and Had Family Phosphatases, PhD Thesis, University of New Mexico, Dec. 2011.
NCBI GenBank Accession No. WP_000985549.1; Multispecies: Sugar phosphatase YidA (Enterobacteriaciaceae), dated Mar. 22, 2015.
Sugar phosphatase YidA, EcoCyc Database Accession No. EG11195, downloaded from Pathway Tools Workshop on Microbial Community Modeling, http://www.ecocyc.org, 2017.
International Search Report, dated Aug. 23, 2016, in International Patent Application No. PCT/KR2016/004894 filed May 10, 2016, 6 pages.
Written Opinion, dated Aug. 23, 2016, in International Patent Application No. PCT/KR2016/004894 filed May 10, 2016, 4 pages.
Hwang et al., "Effect of Increased Glutamate Availability on L-Ornithine Production in Corynebacterium glutamicum", J. Microbiol. Biotechnol., (2008), 18(4) 704-710.
Gu P. et al., One-step of tryptophan attenuator inactivation and promoter swapping to improve the production of L-tryptophan in *Escherichia coli*, Microbial Cell Factories vol. 11, No. 30, pp. 1-9, 2012.
Kuznetsova et al., "Genome-wide Analysis of Substrate Specificities of the *Escherichia coli* Haloacid Dehalogenase-like Phosphatase Family", *Journal of Biological Chemistry*,2006,vol. 281,No. 47,p. 36149-36161.
NCBI, GenBank Accession No. WP_000985549.1, "Multispecies: Sugar Phosphatase YidA [Enterobacteriaceae]", Mar. 22, 2015.
Datsenko et al., "One-step inactivation of chromosomal genes in *Escherichia coli* K-12 using PCT products", *Proc. Natl. Acad. Sci. U.S.A*,2000,vol. 97,No. 12,6640-6645.

(Continued)

*Primary Examiner* — Christian L Fronda
(74) *Attorney, Agent, or Firm* — Knobbe, Martens, Olson & Bear LLP

(57) ABSTRACT

The present disclosure relates to a microorganism of the genus *Escherichia* producing more L-tryptophan by inactivating the activity of phosphatase. Additionally, the present disclosure relates to a method for producing L-tryptophan using the microorganism of the genus *Escherichia*.

4 Claims, No Drawings
Specification includes a Sequence Listing.

(56) References Cited

OTHER PUBLICATIONS

Wang M., Evolution of structure and function among hotdog-fold thioesterases and HAD family phosphatases, University of New Mexico, Doctoral Thesis, pp. 1-127, Dec. 2011.
Office Action issued in Japanese Patent Application No. 2017-555793, dated Sep. 5, 2018.
Office Action issued in Russian Patent Application No. 2017142878, dated Oct. 12, 2018.

* cited by examiner

SEQUENCE LISTING

```
<160> NUMBER OF SEQ ID NOS: 8

<210> SEQ ID NO 1
<211> LENGTH: 270
<212> TYPE: PRT
<213> ORGANISM: Escherichia

<400> SEQUENCE: 1

Met Ala Ile Lys Leu Ile Ala Ile Asp Met Asp Gly Thr Leu Leu Leu
1               5                   10                  15

Pro Asp His Thr Ile Ser Pro Ala Val Lys Asn Ala Ile Ala Ala Ala
                20                  25                  30

Arg Ala Arg Gly Val Asn Val Val Leu Thr Thr Gly Arg Pro Tyr Ala
            35                  40                  45

Gly Val His Asn Tyr Leu Lys Glu Leu His Met Glu Gln Pro Gly Asp
        50                  55                  60

Tyr Cys Ile Thr Tyr Asn Gly Ala Leu Val Gln Lys Ala Ala Asp Gly
65                  70                  75                  80

Ser Thr Val Ala Gln Thr Ala Leu Ser Tyr Asp Asp Tyr Arg Phe Leu
                85                  90                  95

Glu Lys Leu Ser Arg Glu Val Gly Ser His Phe His Ala Leu Asp Arg
            100                 105                 110

Thr Thr Leu Tyr Thr Ala Asn Arg Asp Ile Ser Tyr Tyr Thr Val His
        115                 120                 125

Glu Ser Phe Val Ala Thr Ile Pro Leu Val Phe Cys Glu Ala Glu Lys
    130                 135                 140

Met Asp Pro Asn Thr Gln Phe Leu Lys Val Met Met Ile Asp Glu Pro
145                 150                 155                 160

Ala Ile Leu Asp Gln Ala Ile Ala Arg Ile Pro Gln Glu Val Lys Glu
                165                 170                 175

Lys Tyr Thr Val Leu Lys Ser Ala Pro Tyr Phe Leu Glu Ile Leu Asp
            180                 185                 190

Lys Arg Val Asn Lys Gly Thr Gly Val Lys Ser Leu Ala Asp Val Leu
        195                 200                 205
```

```
Gly Ile Lys Pro Glu Glu Ile Met Ala Ile Gly Asp Gln Glu Asn Asp
        210                 215                 220
Ile Ala Met Ile Glu Tyr Ala Gly Val Gly Val Ala Met Asp Asn Ala
225                 230                 235                 240
Ile Pro Ser Val Lys Glu Val Ala Asn Phe Val Thr Lys Ser Asn Leu
                245                 250                 255
Glu Asp Gly Val Ala Phe Ala Ile Glu Lys Tyr Val Leu Asn
            260                 265                 270

<210> SEQ ID NO 2
<211> LENGTH: 813
<212> TYPE: DNA
<213> ORGANISM: Escherichia
<220> FEATURE:
<221> NAME/KEY: gene
<222> LOCATION: (1)..(813)
<223> OTHER INFORMATION: yidA

<400> SEQUENCE: 2
atggctatta aactcattgc tatcgatatg gatggcaccc ttctgctgcc cgatcacacc       60
atttcacccg ccgttaaaaa tgcgattgcc gcagctcgcg cccgtggcgt gaatgtcgtg      120
ctaacgacgg tcgcccgta tgcaggtgtg cacaactacc tgaaagagct gcatatggaa       180
cagccgggcg actactgcat tacttataac ggcgcgctgg tacagaaggc cgctgatggt      240
agcaccgtgg cgcaaactgc tctcagctat gacgactatc gtttcctgga aaaactctct      300
cgcgaagtcg gttctcattt ccacgccctg accgcacca cgctgtacac gccaaccgt       360 gatatcagct actacacggt gcatgaatcc ttcgttgcca ccattccgct ggtgttctgc      420
gaagcggaga aaatggaccc caatacccag ttcctgaaag tgatgatgat tgatgaaccc      480
gccatcctcg accaggctat cgcgcgtatt ccgcaggaag tgaaagagaa atataccgtg      540
ctgaaaagtg cgccgtactt cctcgaaatc ctcgataaac gcgttaacaa aggtacgggg      600
gtgaaatcac tggccgacgt gttaggtatt aaaccggaag aaatcatggc gattggcgat      660
caggaaaacg atatcgcaat gattgaatat gcaggcgtcg gtgtggcgat ggataacgct      720
attccttcag tgaaagaagt ggcgaacttt gtcaccaaat ctaaccttga agatggcgtg      780
gcgtttgcta ttgagaagta tgtgctgaat taa                                   813

<210> SEQ ID NO 3
<211> LENGTH: 70
<212> TYPE: DNA
<213> ORGANISM: Artificial Sequence
<220> FEATURE:
<223> OTHER INFORMATION: YIDA-CM-F2 Primer

<400> SEQUENCE: 3
aatctacctg gggaactcat ggctattaaa ctcattgcta tcgatatgga aggtgacact       60
atagaacgcg                                                              70

<210> SEQ ID NO 4
<211> LENGTH: 70
<212> TYPE: DNA
<213> ORGANISM: Artificial Sequence
<220> FEATURE:
<223> OTHER INFORMATION: yidA-Cm-R2 Primer

<400> SEQUENCE: 4
cgcccacaga ttaattcagc acatacttct caatagcaaa cgccacgcca tagtggatct       60
gatgggtacc                                                              70
```

<210> SEQ ID NO 5
<211> LENGTH: 70
<212> TYPE: DNA
<213> ORGANISM: Artificial Sequence
<220> FEATURE:
<223> OTHER INFORMATION: yidA-F1 Primer

<400> SEQUENCE: 5
ggtgttgtac tgatttttga gcggaatcgc gttagcatgg gtcaggaacc aatctacctg    60
gggaactcat    70

<210> SEQ ID NO 6
<211> LENGTH: 70
<212> TYPE: DNA
<213> ORGANISM: Artificial Sequence
<220> FEATURE:
<223> OTHER INFORMATION: yidA-R1 Primer

<400> SEQUENCE: 6
gcagtaaacc aataatcagt aagcgggcaa acgcgtttat gctgtttgcc cgcccacaga    60
ttaattcagc    70

<210> SEQ ID NO 7
<211> LENGTH: 20
<212> TYPE: DNA
<213> ORGANISM: Artificial Sequence
<220> FEATURE:
<223> OTHER INFORMATION: yidA conF1 Primer

<400> SEQUENCE: 7
attgatgcgc tctcaccgca    20

<210> SEQ ID NO 8
<211> LENGTH: 20
<212> TYPE: DNA
<213> ORGANISM: Artificial Sequence
<220> FEATURE:
<223> OTHER INFORMATION: yidA conR1 Primer

<400> SEQUENCE: 8
gcctctgggt gaatagtatt    20

MICROORGANISM OF THE GENUS *ESCHERICHIA* PRODUCING L-TRYPTOPHAN AND A METHOD FOR PRODUCING L-TRYPTOPHAN USING THE SAME

CROSS-REFERENCE TO RELATED APPLICATIONS

This application is a U.S. National Phase Application of PCT International Application No. PCT/KR2016/004894, filed on May 10, 2016, designating the United States of America, which is an International Application of and claims the benefit of priority to Korean Patent Application No. 10-2015-0067659, filed on May 14, 2015.

SEQUENCE LISTING STATEMENT

The present application contains a Sequence Listing, which is being submitted via EFS-Web on even date herewith. The Sequence Listing is submitted in a file entitled "Sequence_Listing_HAN030-001APC.txt," which was created on Oct. 30, 2017, and is approximately 6 kb in size. This Sequence Listing is hereby incorporated by reference.

TECHNICAL FIELD

The present disclosure relates to a microorganism of the genus *Escherichia* producing L-tryptophan, in which the activity of phosphatase is modified to be inactivated, and a method for producing L-tryptophan using the microorganism.

BACKGROUND ART

L-tryptophan, which is an essential amino acid, has been widely used as a raw material for pharmaceutical products, such as feed additives, infusion solutions, etc., and has also been widely used as a health food ingredient, etc. L-tryptophan can be produced by a chemical synthesis method, an enzyme reaction method, a fermentation method, etc., but the direct fermentation method using a microorganism is mostly used at present.

A microorganism has an aromatic biosynthetic pathway, in which phosphoenol pyruvate (PEP), which is an intermediate in glycolysis, and erythrose-4-phosphate (E4P), which is a product of the pentose phosphate pathway, initiate polymerization by 3-deoxy-D-arabinoheptulosonate 7-phosphate (DAHP) synthase (EC 2.5.1.54). In the pathway above, PEP and E4P are each conjugated to phosphate, and are substances containing high energy. Further, in the subsequent aromatic biosynthetic pathway, PEP is involved in the reaction when the 5-enolpyruvylshikimate-3-phosphate (EPSP) synthase (EC 2.5.1.19) reaction is carried out, and PRPP is used in the anthranilate phosphoribosyltransferase reaction. Accordingly, it is known that a large amount of high energy substances is required for tryptophan biosynthesis. According to previous studies, it was demonstrated by intracellular quantitative analysis that the highest level of energy is required for biosynthesis of tryptophan from among 20 amino acids (Proc. Natl. Acad. Sci. USA, (2002) V99, pp 3695-3700). Therefore, it can be considered that PEP and E4P play a significant role in strains producing tryptophan at high concentration in terms of continuous supply of precursors and efficient use of energy.

Accordingly, in order to stably supply E4P, the method of increasing the biosynthesis by enhancing the expression of tktA genes (NCBI gene ID: 12931960), which encode transketolase (EC 2.2.1.1), has been used most (Current Opinion in Biotechnology, (2009) V20, pp 651-658). In addition, numerous studies on reducing the use of ATP, which is a high energy substance, are underway in order to maintain intracellular energy level (FEMS Microbiol Lett, (2009) V297, pp 217-224). However, it is still necessary to develop a method for producing L-tryptophan in high efficiency.

DISCLOSURE

Technical Problem

The present inventors have made intensive research efforts to develop a method for efficiently producing L-tryptophan. As a result, the present inventors have developed a method of preserving energy which is unnecessarily wasted while maintaining E4P concentration in cells by preventing decomposition of E4P synthesized in tryptophan-producing strains, and confirmed that the L-tryptophan productivity was improved, thereby completing the present invention.

Technical Solution

An object of the present disclosure is to provide a microorganism of the genus *Escherichia* producing L-tryptophan.

Another object of the present disclosure is to provide a method for producing L-tryptophan using the microorganism producing L-tryptophan.

Advantageous Effects

The present disclosure provides a microorganism of the genus *Escherichia* producing L-tryptophan, wherein the activity of phosphatase comprising an amino acid sequence of SEQ ID NO: 1 is modified to be inactivated, thereby showing an effect that L-tryptophan can be efficiently and economically produced with high yield by using the microorganism above. L-tryptophan produced therefrom can be applied not only to animal feeds or feed additives but also to various products, such as human foods or food additives, drugs, etc.

BEST MODE

An object of the present disclosure is to provide a microorganism of the genus *Escherichia* producing L-tryptophan.

Another object of the present disclosure is to provide a method for producing L-tryptophan using the microorganism producing L-tryptophan.

Solution to Problem

In order to achieve the above object, in an aspect, the present disclosure provides a microorganism of the genus *Escherichia* producing L-tryptophan, wherein the activity of phosphatase comprising an amino acid sequence of SEQ ID NO: 1 is modified to be inactivated. For example, the microorganism of the genus *Escherichia* producing L-tryptophan may be a microorganism in which the L-tryptophan productivity is increased, compared with a microorganism of the genus *Escherichia* producing L-tryptophan in which the endogenous activity of phosphatase is not modified to be inactivated.

As used herein, the term "L-tryptophan" refers to an aromatic L-amino acid, which is an α-amino acid and an essential amino acid not synthesized in vivo having a chemical formula of $C_{11}H_{12}N_2O_2$. In order to increase L-tryptophan productivity in a microorganism, a method of continuously supplying a precursor, i.e., erythrose-4-phosphate (E4P), in tryptophan-producing strains; enhancing the expression of tktA genes to efficiently use energy; increasing the biosynthesis by blocking branch pathways in the biosynthetic pathway; or using less ATP, etc., has been conventionally used.

As used herein, the term "phosphatase" may refer to a protein that catalyzes a reaction for removing a phosphate group from a substrate. The phosphatase of the present invention, which has an amino acid sequence of SEQ ID NO: 1, is a protein encoded by the gene, yidA. In addition, such phosphatase is designated as phosphosugar phosphatase (NCBI gene ID: 12933583) in the NCBI database (http://www.ncbi.nlm.nih.gov), and is also designated as sugar-phosphatase in the EcoCyc database (http://www.ecocyc.org). The protein catalyzes the decomposition of phosphosugar substrates into sugars and phosphoric acids. However, the relevance between the thus-described enzyme and the enhancement of the tryptophan production has not been clarified.

The enzyme described above may include without limitation, in addition to the amino acid sequence represented by SEQ ID NO: 1, any amino acid sequence which has a homology of 70% or higher, specifically 80% or higher, more specifically 90% or higher, even more specifically 95% or higher, yet even more specifically 98% or higher, and yet even still more specifically 99% or higher, to the above amino acid sequence, as long as an enzyme exhibits an effect substantially the same as or corresponding to the enzyme above. Additionally, it is obvious that an enzyme variant having an amino acid sequence with a partial deletion, modification, substitution, or addition also belongs to the scope of the present disclosure, as long as an amino acid sequence has the homology described above and exhibits the effect corresponding to each enzyme.

The genes encoding the phosphatase having an amino acid sequence of SEQ ID NO: 1 may be included without limitation, as long as these have a sequence capable of encoding the enzyme above, and can be represented as yidA genes. Specifically, the genes encoding the enzyme may also include without limitation, in addition to the nucleotide sequence represented by SEQ ID NO: 2, any gene sequence encoding the enzyme, which has a homology to 80% or higher, specifically 90% or higher, more specifically 95% or higher, even more specifically 98% or higher, and yet even more specifically 99% or higher, to the above nucleotide sequence, as long as the gene sequence encodes an enzyme which exhibits an effect substantially the same as or corresponding to the enzyme above. Additionally, it is obvious that any nucleotide sequence which has the homology described above can belong to the scope of the present disclosure, although the nucleotide sequence may have a partial deletion, modification, substitution, or addition therein.

As used herein, the term "homology" refers to a percentage of identity between two polynucleotide or polypeptide moieties. Sequence correspondence from one moiety to another may be determined by a known technique in the art. For example, homology may be determined by directly aligning the sequence information (e.g., parameters such as score, identity, and similarity) on two polynucleotide molecules or two polypeptide molecules using a computer program (e.g., BLAST 2.0) that is readily available and capable of aligning sequence information. Additionally, homology between polynucleotides may be determined by hybridizing the polynucleotides under the condition for forming a stable double-strand in the homologous regions and then digesting the hybridized strand by a single-strand-specific nuclease to determine the size of digested fragments.

As used herein, the term "endogenous activity" refers to an active state of an enzyme in a microorganism in a natural state or before modification.

As used herein, the term "modified to be inactivated" refers to a case when the gene encoding an enzyme is not expressed at all and/or a case when the gene is expressed but exhibits no activity or a decrease in activity compared to that of the native strain or the strain before modification.

The inactivation of the activity of an enzyme compared to its endogenous activity refers to a case where there is no activity or a decrease in activity of an enzyme in a microorganism compared with that originally possessed in its natural state or before modification. The decrease in activity refers to a concept including a case where the activity of an enzyme itself is lower than that of an enzyme originally possessed in a microorganism due to modification of the gene encoding the enzyme, a case where the level of overall enzyme activity in cells is lower than that of the native strain or that of the strain before modification due to inhibition of expression or inhibition of translation of the gene encoding the same, or a combined case thereof.

The method of modifying such enzyme activity for inactivation may be achieved by various well-known methods in the art. Examples of the methods may include a method of substituting the gene encoding the enzyme on the chromosome with a gene mutated so that the enzyme activity can be reduced, including the case when the enzyme activity is eliminated; a method of deleting part or the entirety of the gene encoding the enzyme; a method of substituting the expression control sequence of the gene encoding the enzyme with a sequence having weak or no activity; a method of introducing a modification into the expression control sequence of the gene on the chromosome encoding the enzyme; a method of deleting part or the entirety of the gene on the chromosome encoding the enzyme; a method of introducing an antisense oligonucleotide (e.g., antisense RNA), which inhibits the translation from the mRNA into an enzyme by a complementary binding to the transcript of the gene on the chromosome; a method of making the attachment of a ribosome impossible by forming a secondary structure by artificially adding a Shine-Dalgarno (SD) sequence and its complementary sequence on the front end of the SD sequence of the gene encoding the enzyme; a method of reverse transcription engineering (RTE), which adds a promoter to be reversely transcribed on the 3' terminus of the open reading frame (ORF) of the corresponding sequence, etc., and may also include a combination thereof, but are not particularly limited thereto.

Specifically, the method of deleting part or the entirety of a gene encoding the enzyme may be performed by substituting a polynucleotide encoding an endogenous target protein within the chromosome with a polynucleotide or a marker gene having a partial deletion in the nucleic acid sequence, using a vector for chromosomal insertion in bacteria. In an exemplary embodiment of the method for deleting part or the entirety of a gene, a method of deleting the gene by homologous recombination may be used.

As used herein, the term "part", although it may vary depending on the types of polynucleotides, may specifically refer to 1 nucleotide to 300 nucleotides, more specifically 1 nucleotide to 100 nucleotides, and even more specifically 1 nucleotide to 50 nucleotides, but is not particularly limited thereto.

As used herein, the term "homologous recombination" refers to genetic recombination that occurs via crossover at genetic chain loci having mutual homology.

Specifically, the method of modifying the expression control sequence may be carried out by inducing a modification of the expression control sequence via deletion, insertion, non-conservative or conservative substitution, or a combination thereof in the nucleic acid sequence of the expression control sequence; or by substituting with a weaker promoter, etc. The expression control sequence may include a promoter, an operator sequence, a sequence encoding a ribosome-binding region, and sequences controlling the termination of transcription and translation.

Furthermore, the method of modifying the gene sequence on the chromosome may be carried out by inducing a modification in the sequence by deletion, insertion, non-conservative or conservative substitution, or a combination thereof in the gene sequence for further weakening the enzyme activity; or by substituting with a gene sequence which was improved to have weaker activity or a gene sequence which was improved to have no activity.

According to an exemplary embodiment of the present disclosure, in order to inactivate the endogenous activity of phosphatase having the amino acid sequence of SEQ ID NO: 1, it was found that the L-tryptophan productivity in various *Escherichia coli* producing L-tryptophan, in which the gene, yidA, encoding the phosphatase is deleted, was increased compared with the parent strains in which yidA is not deleted. Therefore, it was confirmed that a microorganism of the genus *Escherichia* producing L-tryptophan, in which the endogenous activity of phosphatase is modified to be inactivated, was able to efficiently produce L-tryptophan.

In the present invention, the microorganism producing L-tryptophan refers to a microorganism capable of producing L-tryptophan from a carbon source in the media above. Additionally, the microorganism producing L-tryptophan may be a recombinant microorganism. Specifically, the types of the microorganism are not particularly limited as long as a microorganism can produce L-tryptophan. However, the microorganism may be a microorganism belonging to the genera *Enterobacter, Escherichia, Erwinia, Serratia, Providencia, Corynebacterium*, and *Brevibacterium*, and specifically a microorganism belonging to the genus *Escherichia*.

More specifically, the microorganism of the genus *Escherichia* may specifically be *Escherichia coli*. However, any microorganisms belonging to the genus *Escherichia* which can increase the L-tryptophan productivity by inactivating the phosphatase activity can be included without limitation.

Specifically, the parent strain of the microorganism of the genus *Escherichia* producing L-tryptophan by inactivation of the phosphatase activity may not be particularly limited as long as the microorganism has tryptophan productivity. For example, the microorganism producing tryptophan may be a microorganism in which, for enhancing the tryptophan biosynthetic pathway, the activities of the gene in the competitive pathway, the regulator in the directional pathway of tryptophan operon, and the gene for introducing and decomposing tryptophan were weakened or inactivated, and/or the activity of the tryptophan operon was overexpressed. The method of weakening or inactivating the activity are the same as explained above, and the methods known in the art may be included without limitation. Additionally, the methods for overexpressing the activity of tryptophan operon known in the art are included without limitation. For example, the methods may include a method of further inserting a polynucleotide, which includes part or the entirety of the nucleotide sequence of the operon gene or an expression control region introduced from outside, into the chromosome; a method of increasing the copy number by introducing into a vector system; a method of enhancing operon activity by substituting the expression control sequence that controls gene expression with another expression control sequence, a modification having an induced mutation in part or the entirety of the nucleotide sequence of the expression control region, and an introduction of a modification of the gene itself, etc., but are not limited thereto. Specifically, the microorganism may be *Escherichia coli*, in which part or the entirety of the pheA gene, trpR gene, mtr gene, and/or tnaAB gene are deleted and/or the tryptophan is overexpressed.

In the present disclosure, in addition to pheA gene, trpR gene, mtr gene, tnaAB gene, and tryptophan operon, and protein sequences encoded by them, the DNA and protein sequences used in the present disclosure may be obtained from a known database, e.g., GenBank of NCBI, but are not limited thereto. Additionally, the specific details with respect to pheA gene, trpR gene, mtr gene, tnaAB gene, etc. may be found in the disclosures of Korean Patent No. 10-0792095 and Korean Patent Publication No. 10-2013-0082121, and the entirety of the specifications of the same may be included as references of the present disclosure.

From the exemplary embodiments of the present disclosure, it was confirmed that, as a result of inactivating the activity of phosphatase in various parent strains, any microorganism of the genus *Escherichia* producing L-tryptophan, regardless of its parent strain, had significantly improved L-tryptophan productivity when the phosphatase activity was inactivated.

In another aspect, the present disclosure provides a method for producing L-tryptophan, comprising culturing the microorganism of the genus *Escherichia* of the present disclosure producing L-tryptophan, in which the activity of phosphatase comprising an amino acid sequence of SEQ ID NO: 1 is modified to be inactivated, in a medium; and recovering L-tryptophan from the cultured medium or the cultured microorganism.

The medium and other culture conditions used for culturing the microorganism of the present disclosure are not particularly limited but any medium used for the conventional cultivation of the microorganism of the genus *Escherichia* may be used. Specifically, the microorganism of the present disclosure may be cultured in a conventional medium containing appropriate carbon sources, nitrogen sources, phosphorous sources, inorganic compounds, amino acids and/or vitamins, etc., in an aerobic condition while adjusting temperature, pH, etc.

Examples of the carbon sources to be used in the present disclosure may include carbohydrates such as glucose, fructose, sucrose, maltose, mannitol, sorbitol, etc.; alcohols such as sugar alcohols, glycerol, pyruvate, lactate, citrate, etc.; and amino acids such as organic acid, glutamic acid, methionine, lysine, etc. Additionally, natural organic nutrients such as starch hydrolysate, molasses, blackstrap molasses, rice bran, cassava starch, sugar cane molasses, corn steep liquor, etc., and specifically, carbohydrates such as glucose and sterile pretreated molasses (i.e., molasses converted to a reducing sugar), etc. Furthermore, various other carbon sources in a suitable amount may be used without limitation.

These carbon sources may be used alone or in a combination of two or more, but are not limited thereto.

Examples of the nitrogen sources to be used in the present disclosure may include inorganic compounds such as ammonia, ammonium sulfate, ammonium chloride, ammonium acetate, ammonium phosphate, ammonium carbonate, ammonium nitrate, etc.; amino acids such as glutamic acid, methionine, glutamine, etc.; and organic nitrogen sources such as peptone, NZ-amine, meat extract, yeast extract, malt extract, corn steep liquor, casein hydrolysate, fish or decomposition products thereof, defatted soybean cake or decomposition products thereof, etc. These nitrogen sources may be used alone or in a combination of two or more, but are not limited thereto.

Examples of the phosphorus sources to be used in the present application may include potassium phosphate monobasic, dipotassium phosphate dibasic, corresponding sodium-containing salts, etc., but are not limited thereto. Examples of inorganic compounds may include sodium chloride, calcium chloride, iron chloride, magnesium sulfate, manganese sulfate, calcium carbonate, etc., and additionally, amino acids, vitamins, and/or suitable precursors for a culture medium may be included. These media or precursors may be added to a culture by a batch culture or continuous culture.

In the present disclosure, the pH of a culture may be adjusted during the culture by adding a compound such as ammonium hydroxide, potassium hydroxide, ammonia, phosphoric acid, and sulfuric acid to the culture in an appropriate manner. Additionally, during the cultivation, an anti-foaming agent such as a fatty acid polyglycol ester may be used to inhibit the formation of foam. Additionally, oxygen or an oxygen-containing gas may be injected into the culture in order to maintain an aerobic state of the culture; or nitrogen, hydrogen, or carbon dioxide gas may be injected without the injection of a gas in order to maintain an anaerobic or microaerobic state of the culture.

The culture temperature may generally be in a range from 27° C. to 40° C., and specifically, from 30° C. to 37° C., but is not limited thereto. The cultivation may be continued until the desired amount of useful materials are obtained, and specifically for from 10 hours to 100 hours, but the cultivation time is not limited thereto.

L-Tryptophan may be recovered by a suitable method known in the art, e.g., batch culture, continuous culture, or fed batch culture, etc., according to the cultivation method of the present disclosure.

The recovery may also include a step of purification. The step of purification can purify L-tryptophan recovered using a suitable method known in the art.

Mode for Invention

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Preparation of yidA-Deficient Wild-Type Strain

In the Example, preparation of a strain in which the activity of phosphatase is inactivated from a strain producing L-tryptophan was attempted.

In order to enhance the tryptophan productivity in the W3110 strain, an *Escherichia coli* wild-type strain, i.e., a representative microorganism of the genus *Escherichia*, the yidA gene encoding phosphatase was deleted by homologous recombination from the W3110 trpΔ2 strain (Korean Patent Publication No. 10-2013-0082121), in which the tryptophan productivity was enhanced and in which the tnaAB gene in the form of an operon of the pheA gene (NCBI gene ID: 12934467) encoding chorismate mutase/prephenate dehydratase (CM-PDT), the tnaA gene (NCBI gene ID: 12933600) encoding tryptophanase, and the tnaB gene (NCBI gene ID: 12933602) encoding a tryptophan importer were deleted.

Specifically, for the deletion of the gene, yidA, having the nucleotide sequence of SEQ ID NO: 2, the one-step inactivation method using lambda Red recombinase developed by Datsenko K A et al. was employed (Proc Natl Acad Sci USA, (2000) 97:6640-6645). As a marker for confirming the gene insertion, an rmf promoter was ligated to pUC19 (New England Biolabs (USA)), and the chloramphenicol gene of pUCprmfmloxP obtained by ligating the mutant, loxP-$Cm^R$-loxP cassette, which was obtained from pACYC184 (New England Biolab), was used (Korean Patent Publication No. 10-2009-0075549).

First, primary polymerase chain reaction (hereinafter referred to as PCR) was performed using pUCprmfmloxP as a template and primer combinations of SEQ ID NOs: 3 and 4 having a part of the yidA gene and a partial nucleotide sequence of the chloramphenicol-resistant gene of the pUCprmfmloxP gene under the conditions of 30 cycles of denaturation at 94° C. for 30 seconds, annealing at 55° C. for 30 seconds, and elongation at 72° C. for 1 minute, thereby obtaining ΔyidA1st (about 1.2 kb), a PCR product. Thereafter, ΔyidA1st (1.2 kb), the PCT product, obtained by PCR was electrophoresed on a 0.8% agarose gel eluted, and then used as a template for secondary PCR. The secondary PCR was performed using the eluted primary PCR product as a template and the primer combinations of SEQ ID NOs: 5 and 6 containing nucleotide sequences of 20 bp of the 5' and 3' regions of the PCR product obtained in the primary PCR under the conditions of 30 cycles of denaturation at 94° C. for 30 seconds, annealing at 55° C. for 30 seconds, and elongation at 72° C. for 1 minute, thereby obtaining ΔyidA (about 1.3 kb), a PCR product. The thus-obtained PCR product was electrophoresed on a 0.8% agarose gel, eluted, and then used in recombination.

*E. coli* W3110 trpΔ2, which was transformed with a pKD46 vector according to the one-step inactivation method developed by Datsenko K A et al. (Proc Natl Acad Sci USA., (2000) 97:6640-6645), was prepared as a competent strain, and transformation was performed by introducing the gene fragment, ΔyidA (1.3 kb) obtained by primary and secondary PCR. The strains were cultured on the LB medium containing chloramphenicol, and then primary transformants having chloramphenicol resistance were selected.

After removal of pKD46 from the thus-obtained primary recombinant strains having chloramphenicol resistance, a pJW168 vector (Gene, (2000) 247, 255-264) was introduced therein so as to remove the chloramphenicol marker gene from the strains (Gene, (2000) 247, 255-264). PCR was performed using primers of SEQ ID NOs: 7 and 8 to obtain a PCR product (about 0.5 kb), indicating that the strains finally obtained had deletion of the yidA gene. The strains having the deletion of such gene were designated as W3110 trpΔ2 yidA.

The sequences of the primers used in the Example are listed in Table 1 below.

TABLE 1

| Primer | Sequence | SEQ ID NO: |
|---|---|---|
| yidA-Cm-F2 | aatctacctggggaactcATGgctattaaactcattgcta tcgatatggaAggTgACACTATAgAACgCg | 3 |
| yidA-Cm-R2 | cgcccacagaTTAattcagcacatacttctcaatagcaaa cgccacgccaTAgTggATCTgATgggTACC | 4 |
| yidA-F1 | ggtgttgtactgattttgagcggaatcgcgttagcatgg gtcaggaaccaatctacctggggaactcAT | 5 |
| yidA-F1 | gcagtaaaccaataatcagtaagcgggcaaacgcgtttat gctgtttgcccgcccacagaTTAattcagc | 6 |
| yidA conF1 | ATTGATGCGCTCTCACCGCA | 7 |
| yidA conR1 | GCCTCTGGGTGAATAGTATT | 8 |

Example 2: Preparation of Tryptophan-Producing Strain in which Phosphatase is Inactivated In the Example, KCCM11166P (Korean Patent No. 10-1261147), which is an another representative *Escherichia coli* producing tryptophan, was used as the parent strain, and the yidA gene encoding phosphatase was deleted by homologous recombination in the same manner as described in Example 1.

It was confirmed that the strains finally obtained had deletion of the yidA gene due to the PCR product (about 0.5 kb) which was obtained by PCR using the primers of SEQ ID NOs: 7 and 8, and then the strains were designated as CA04-2805.

Example 3: Evaluation of Tryptophan Productivity in yidA-Deficient Wild-Type Strain In order to compare the tryptophan productivity of W3110 trpΔ2 yidA, prepared in Example 1, and W3110 trpΔ2, which is the parent strain, pCL-Dtrp_att-trpEDCBA and pBAC-Dtrp_att-trpDCBA were introduced into each strain by the transformation method. The introduced vectors were vectors in which the expression of tryptophan operon was enhanced such that tryptophan can be produced in excess because the control mechanism in the tryptophan operon control region was released (Korean Patent Publication No. 10-2013-0082121). The vector-introduced strains were cultured on a tryptophan test medium prepared according to the composition listed in Table 2 below, and their L-tryptophan productivity was compared.

TABLE 2

Composition of the tryptophan test medium

| Composition | Concentration (per liter) |
|---|---|
| Glucose | 2 g |
| K$_2$HPO$_4$ | 1 g |
| (NH$_4$)$_2$SO$_4$ | 12 g |
| NaCl | 1 g |
| Na$_2$HPO$_4$•H$_2$O | 5 g |
| MgSO$_4$•H$_2$O | 1 g |
| MnSO$_4$•H$_2$O | 15 mg |
| CuSO$_4$•H$_2$O | 3 mg |
| ZnSO$_4$•H$_2$O | 30 mg |

TABLE 2-continued

Composition of the tryptophan test medium

| Composition | Concentration (per liter) |
|---|---|
| Sodium citrate | 1 g |
| Yeast extract | 1 g |
| Phenylalanine | 0.15 g |
| pH | 6.8 |

One platinum loop of each of the strains cultured overnight on the LB solid medium in an incubator at 37° C. was inoculated into the test medium (25 mL) of Table 2. Thereafter, the resultants were cultured in an incubator at 37° C. and 200 rpm for 48 hours to compare tryptophan concentration (Table 3).

TABLE 3

| Strain | Tryptophan concentration (g/L) |
|---|---|
| W3110 trpΔ2/pCL-Dtrp_att-trpEDCBA, pBAC-Dtrp_att-trpDCBA | 0.5 |
| W3110 trpΔ2 yidA/pCL-Dtrp_att-trpEDCBA, pBAC-Dtrp_att-trpDCBA | 0.7 |

The results above showed that the tryptophan productivity in the strain, in which the activity of phosphatase encoded by the gene yidA was inactivated, was increased by 40% as compared with the strain in which the activity of phosphatase was not inactivated. Therefore, it was confirmed that the tryptophan productivity could be improved by inactivation of phosphatase encoded by yidA. From such results, it can be interpreted that the degradation of E4P, an important precursor for tryptophan biosynthesis, was inhibited, and thereby the E4P concentration in the cells was maintained. As a result, energy that is unnecessarily wasted is preserved and used in the tryptophan biosynthesis.

Example 4: Evaluation of Tryptophan Productivity in yidA-Deficient Strain

In order to measure the tryptophan titer of the yidA-deficient strain (CA04-2805) prepared in Example 2 and the parent strain (KCCM11166P), the strains were cultured in the tryptophan titer medium prepared according to the compositions listed in Table 4, and then improvement of L-tryptophan production efficiency was confirmed.

TABLE 4

Composition in tryptophan titer medium

| Composition | Concentration (per liter) |
|---|---|
| Glucose | 60 g |
| K$_2$HPO$_4$ | 1 g |
| (NH$_4$)2SO$_4$ | 10 g |
| NaCl | 1 g |
| MgSO$_4$•7H$_2$O | 1 g |
| Sodium citrate | 5 g |
| Yeast extract | 2 g |
| Calcium carbonate | 40 g |
| Phenylalanine | 0.15 g |
| Tyrosine | 0.1 g |
| pH | 6.8 |

One platinum loop of each of *E. coli* KCCM11166P and *E. coli* CA04-2805 cultured overnight on the LB solid medium in an incubator at 37° C. was inoculated into the titer medium (25 mL) of Table 4. Thereafter, the resultants were cultured in an incubator at 37° C. and 200 rpm for 48 hours to compare glucose consumption rate and tryptophan concentration.

As a result, as described in Table 5 below, it was confirmed that the tryptophan concentration of CA04-2805, the strain in which the activity of phosphatase encoded by the yidA gene was inactivated, was increased by about 10% compared to that of KCCM11166P, the parent strain which was a control.

TABLE 5

| Strain | Tryptophan concentration (g/L) |
|---|---|
| KCCM11166P | 7.48 |
| CA04-2805 | 8.23 |

The present inventors have confirmed that the KCCM11166P-based strain, which is the yidA-deficient strain in which the activity of phosphatase was inactivated, has an improved tryptophan-producing ability, and named the strain as "CA04-2805" or "CA04-2805 (KCCM11166P_ΔyidA)" and deposited it to the KCCM on Dec. 5, 2014, where it was assigned the deposit number KCCM11636P.

The results above suggest that in the microorganism of the present disclosure of the genus *Escherichia* producing tryptophan, the strain which inactivates the phosphatase activity can improve the L-tryptophan-producing ability compared to unmodified strain to be inactivated.

While the present disclosure has been described with reference to the particular illustrative embodiments, it will be understood by those skilled in the art to which the present disclosure pertains that the present invention may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. A modified microorganism of the genus *Escherichia* having increased production of L-tryptophan compared to an unmodified microorganism, wherein the activity of phosphatase comprising the amino acid sequence of SEQ ID NO: 1 is modified to be inactivated.

2. The microorganism according to claim 1, wherein the microorganism of the genus *Escherichia* is *Escherichia coli*.

3. A method for producing L-tryptophan, comprising:
(i) culturing the microorganism of the genus *Escherichia* of claim 1 in a medium; and
(ii) recovering L-tryptophan from the cultured medium or the cultured microorganism.

4. A method for producing L-tryptophan, comprising:
(i) culturing the microorganism of the genus *Escherichia* of claim 2 in a medium; and
(ii) recovering L-tryptophan from the cultured medium or the cultured microorganism.

* * * * *